(12) United States Patent
Li et al.

(10) Patent No.: US 11,813,117 B2
(45) Date of Patent: Nov. 14, 2023

(54) ULTRASOUND IMAGING METHOD AND ULTRASOUND IMAGING DEVICE

(71) Applicant: SHENZHEN MINDRAY BIO-MEDICAL ELECTRONICS CO., LTD., Guangdong (CN)

(72) Inventors: Shuangshuang Li, Shenzhen (CN); Zebing Wang, Shenzhen (CN)

(73) Assignee: Shenzhen Mindray Bio-Medical Electronics Co., Ltd., Shenzhen (CN)

( * ) Notice: Subject to any disclaimer, the term of this patent is extended or adjusted under 35 U.S.C. 154(b) by 23 days.

(21) Appl. No.: 17/068,744

(22) Filed: Oct. 12, 2020

(65) Prior Publication Data
US 2021/0022712 A1    Jan. 28, 2021

Related U.S. Application Data

(63) Continuation of application No. PCT/CN2018/083010, filed on Apr. 13, 2018.

(51) Int. Cl.
*A61B 8/08* (2006.01)
*A61B 8/00* (2006.01)
*G01S 7/52* (2006.01)

(52) U.S. Cl.
CPC .............. *A61B 8/485* (2013.01); *A61B 8/461* (2013.01); *A61B 8/5246* (2013.01); *A61B 8/54* (2013.01); *G01S 7/52085* (2013.01)

(58) Field of Classification Search
CPC ....... A61B 8/485; A61B 8/461; A61B 8/5246; A61B 8/54; G01S 7/52085
See application file for complete search history.

(56) References Cited

U.S. PATENT DOCUMENTS

| 5,301,670 A | * | 4/1994 | Sato | .................... G01S 15/8979 600/455 |
| 9,672,595 B2 | | 6/2017 | Murashita | |
| 10,548,572 B2 | | 2/2020 | Susumu | |

(Continued)

FOREIGN PATENT DOCUMENTS

| CN | 101732073 A | 6/2010 |
| CN | 102283679 A | 12/2011 |

(Continued)

OTHER PUBLICATIONS

PCT International Search Report and the Written Opinion dated Dec. 29, 2018, issued in related International Application No. PCT/CN2018/083010, with English translation (14 pages).

(Continued)

*Primary Examiner* — Katherine L Fernandez
*Assistant Examiner* — Brooke Lyn Klein
(74) *Attorney, Agent, or Firm* — Sheppard Mullin Richter & Hampton LLP

(57) ABSTRACT

Ultrasound imaging methods and ultrasound imaging devices are provided, in which an inter-frame processing may be performed on elasticity echo data or the elasticity images to obtain new elasticity images, thereby improving the display frame rate of the elasticity images. The elasticity echo data comprises an ultrasound echo of an ultrasound wave returned from an object, and the elasticity images comprises at least two frames and obtained according to the elasticity echo data.

11 Claims, 3 Drawing Sheets

(56) References Cited

U.S. PATENT DOCUMENTS

| | | | |
|---|---|---|---|
| 2007/0016029 A1* | 1/2007 | Donaldson | A61B 8/565 |
| | | | 600/437 |
| 2008/0285819 A1 | 11/2008 | Konofagou et al. | |
| 2010/0130861 A1 | 5/2010 | Shimazaki | |
| 2011/0077518 A1 | 3/2011 | Miyachi | |
| 2013/0090560 A1* | 4/2013 | Kotaki | A61B 8/461 |
| | | | 600/443 |
| 2015/0087980 A1* | 3/2015 | Yao | G01S 7/52042 |
| | | | 600/440 |
| 2017/0079619 A1 | 3/2017 | Srinivasan | |
| 2017/0112471 A1* | 4/2017 | Toji | A61B 8/4254 |
| 2020/0297320 A1 | 9/2020 | Specht et al. | |

FOREIGN PATENT DOCUMENTS

| | | |
|---|---|---|
| CN | 102378010 A | 3/2012 |
| CN | 102525552 A | 7/2012 |
| CN | 104135937 A | 11/2014 |
| JP | 2016-158922 A | 9/2016 |

OTHER PUBLICATIONS

PCT International Preliminary Report on Patentability dated Oct. 22, 2020, issued in related International Application No. PCT/CN2018/083010, with English translation (11 pages).

First Search dated Mar. 11, 2022, issued in related Chinese Application No. 201880060582.9 (1 page).

\* cited by examiner

ULTRASOUND IMAGING METHOD AND ULTRASOUND IMAGING DEVICE

CROSS-REFERENCE TO RELATED APPLICATION

This application is a continuation application of International Patent Application No. PCT/CN2018/083010, filed with the China National Intellectual Property Administration (CNIPA) of People's Republic of China on Apr. 13, 2018, and entitled "ULTRASOUND IMAGING METHOD AND ULTRASOUND IMAGING EQUIPMENT". The entire content of the above-identified application is incorporated herein by reference.

TECHNICAL FIELD

The present disclosure relates to medical ultrasound imaging, in particular to an ultrasound imaging method and an ultrasound imaging device.

BACKGROUND

Ultrasound elastography is one of the hotspots of clinical research in recent years. It mainly reflects the elasticity and softness of tissues, and has been used increasingly in the auxiliary detection, discrimination of benign and prognostic evaluation of tissue cancer. According to different imaging principles, ultrasound elastography technologies are classified mainly into two categories: strain elastography technology and shear-wave elastography technology.

In the strain elastography method, a certain deformation is generated by pressing the tissue with a probe, and then the parameters related to the elasticity of the tissue, such as the strain or the strain rate, may be calculated and imaged, so as to indirectly represent the elastic difference between different tissues. Because the strain parameters are sensitive to pressure, the pressure applied by the probe in this method needs to be as uniform and stable as possible, which puts higher requirements on the operator's technique. In the shear wave elastography method, the shear wave is generated, and propagates in the tissue, and the propagation parameter (such as the propagation speed) is detected so as to represent the hardness difference between the tissues. Because it no longer relies on the operator's specific pressure on the tissue, this elastography method has improved stability and repeatability, and the quantitative measurement results make the doctor's diagnosis more convenient and objective.

The shear wave elastography method based on acoustic radiation force is a commonly used method in the market. In this method, special ultrasound pulses are transmitted into the tissue to generate, based on the acoustic radiation force effect, the shear wave propagating in the tissue, and the propagation process of the shear wave is detected by the ultrasound sequence, so as to calculate the parameter related to the elasticity of the tissue. In this method, real-time image display can be achieved. However, due to the safety output limitation of ultrasound energy, the actual refresh frame rate of the elasticity images is low.

SUMMARY

The present disclosure provides ultrasound imaging methods and ultrasound imaging devices, in which a new elasticity image may be generated by performing an inter-frame processing on the obtained elastic echo data or the elasticity images, thereby improving the display frame rate of the elasticity images.

In one embodiment, an ultrasound imaging method is provided, which may include:
transmitting a first ultrasound wave to a target area of an object to be examined to track a shear wave propagating in the target area;
receiving an ultrasound echo of the first ultrasound wave returned from the target area to obtain a first echo data;
obtaining a first elasticity image frame sequence of the target area according to the first echo data, where the first elasticity image frame sequence includes at least two frames of elasticity images; and
performing an inter-frame processing, where the inter-frame processing includes generating at least one frame of additional elasticity image according to the at least two frames of elasticity images so as to obtain a second elasticity image frame sequence and displaying the second elasticity image frame sequence, where a number of frames of the second elasticity image frame sequence is greater than a number of frames of the first elasticity image frame sequence.

In one embodiment, an ultrasound imaging method is provided, which may include:
displaying a first elasticity image frame sequence, where the first elasticity image frame sequence includes at least two frames of elasticity images;
receiving a first operation, and performing an inter-frame processing according to the first operation;
where the inter-frame processing includes generating at least one frame of additional elasticity image according to the at least two frames of elasticity images so as to obtain a second elasticity image frame sequence and displaying the second elasticity image frame sequence, where a number of frames of the second elasticity image frame sequence is greater than a number of frames of the first elasticity image frame sequence.

In one embodiment, an ultrasound imaging method is provided, which may include:
transmitting a first ultrasound wave to a target area of an object to be examined, and receiving an ultrasound echo of the first ultrasound wave returned from the target area to obtain a first echo data;
obtaining a first image frame sequence of the target area in a first mode according to the first echo data;
transmitting a second ultrasound wave to the target area of the object to be examined, and receiving an ultrasound echo of the second ultrasound wave returned from the target area to obtain a second echo data;
obtaining a second image frame sequence of the target area in a second mode according to the second echo data;
generating at least one frame of additional image in the first mode according to the first image frame sequence and the second image frame sequence so as to obtain a third image frame sequence in the first mode, where a number of frames of the third image frame sequence is greater than a number of frames of the first image frame sequence; and
displaying the third image frame sequence in the first mode.

In one embodiment, an ultrasound imaging device is provided, which may include:
an ultrasound probe;
a transmitting/receiving sequence controller which is configured to excite the ultrasound probe to transmit a first ultrasound wave to a target area of an object to be examined to track a shear wave propagating in the target area and receive an ultrasound echo of the first ultrasound wave returned from the target area to obtain a first echo data; and a processor which is configured to obtain a first elasticity image frame sequence of the target area according to the first echo data and perform an inter-frame processing, where the first elasticity image frame sequence includes at least two frames of elasticity images;

where the inter-frame processing includes generating at least one frame of additional elasticity image according to the at least two frames of elasticity images so as to obtain a second elasticity image frame sequence, and displaying the second elasticity image frame sequence, where a number of frames of the second elasticity image frame sequence is greater than a number of frames of the first elasticity image frame sequence.

In one embodiment, an ultrasound imaging device is provided, which may include:

a display which is configured to display a first elasticity image frame sequence, where the first elasticity image frame sequence includes at least two frames of elasticity images; and a processor which is configured to receive a first operation, and perform an inter-frame processing according to the first operation;

where the inter-frame processing includes generating at least one frame of additional elasticity image according to the at least two frames of elasticity images so as to obtain a second elasticity image frame sequence and displaying the second elasticity image frame sequence, where a number of frames of the second elasticity image frame sequence is greater than a number of frames of the first elasticity image frame sequence.

In one embodiment, an ultrasound imaging device is provided, which may include:

an ultrasound probe;

a transmitting/receiving sequence controller which is configured to excite the ultrasound probe to transmit a first ultrasound wave to a target area of an object to be examined, and receive an ultrasound echo of the first ultrasound wave returned from the target area to obtain a first echo data;

a processor which is configured to obtain a first image frame sequence of the target area in a first mode according to the first echo data;

where the transmitting/receiving sequence controller is further configured to excite the ultrasound probe to transmit a second ultrasound wave to the target area of the object to be examined, and receive an ultrasound echo of the second ultrasound wave returned from the target area to obtain a second echo data;

and where the processor is further configured to obtain a second image frame sequence of the target area in a second mode according to the second echo data, and generate at least one frame of additional image in the first mode according to the first image frame sequence and the second image frame sequence so as to obtain a third image frame sequence in the first mode, where a number of frames of the third image frame sequence is greater than a number of frames of the first image frame sequence; and a display which is configured to display the third image frame sequence in the first mode.

In the technical solutions provided by the embodiments of the present disclosure, the first ultrasound waves may be transmitted to the target area of the object to be examined to track the shear wave propagating in the target area; the ultrasound echoes of the first ultrasound waves returned from the target area may be received to obtain the first echo data; the first elasticity image frame sequence of the target area may be obtained according to the first echo data; and at least one additional elasticity image may be generated according to the at least two frames of elasticity images, so as to obtain a second elasticity image frame sequence, and the second elasticity image frame sequence may be displayed. Since after the inter-frame processing process the number of frames of the obtained second elasticity image frame sequence is greater than the number of frames of the original first elasticity image frame sequence, the display frame rate of the obtained second elasticity image frame sequence is higher than the display frame rate of the original first elasticity image frame sequence, thereby increasing the display frame rate of the elasticity images.

DETAILED DESCRIPTION

The technical solutions in the embodiments of the present disclosure will be clearly and completely described below in conjunction with the drawings. Obviously, the described embodiments are only a part, but not all, of the embodiments of the present disclosure.

The terms "first", "second", "third", "fourth", etc. (if any) in the specification, claims and drawings of the present disclosure are used to distinguish similar objects, but not to describe a specific order or sequence. It should be understood that the data used in this way can be interchanged under appropriate circumstances so that the embodiments described herein can be implemented in an order other than the order illustrated or described herein. In addition, the terms "including" and "having" and any variations thereof are intended to mean non-exclusive inclusion. For example, a process, method, system, product or device that includes a series of steps or units is not necessarily limited to the clearly listed steps or units, but may include other steps or units that are not clearly listed or are inherent to the process, method, product or device.

Figure 1:
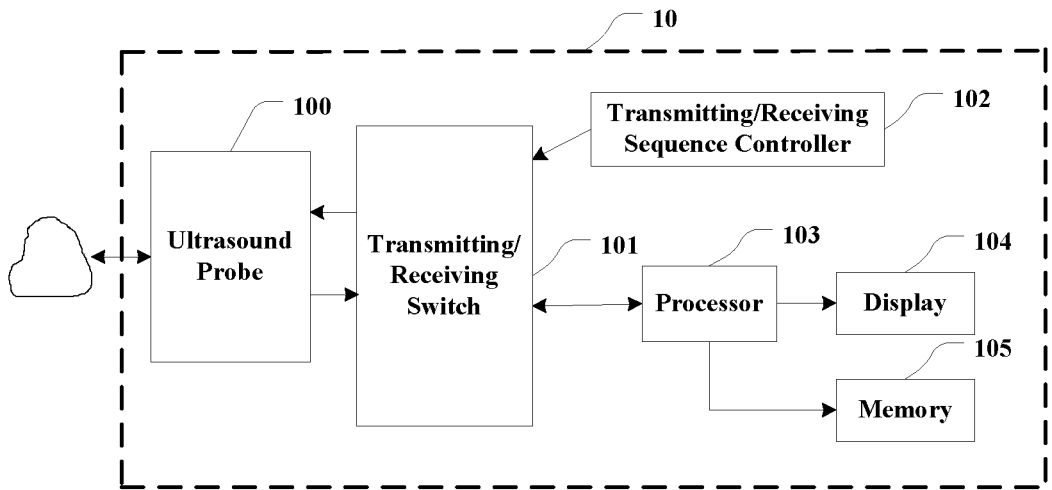
FIG. 1 is a schematic block diagram of the ultrasound imaging device in one embodiment.

FIG. 1 is a schematic block diagram of an ultrasound imaging device 10 in one embodiment of the present disclosure. The ultrasound imaging device 10 may include an ultrasound probe 100, a transmitting/receiving switch 101, a transmitting/receiving sequence controller 102, a processor 103 and a display 104. The transmitting/receiving sequence controller 102 may excite the ultrasound probe 100 to transmit the ultrasound waves to the target object, and may control the ultrasound probe 100 to receive the ultrasound echoes returned from the target object, thereby obtaining the ultrasound echo signals. The processor 103 may process the ultrasound echo signals to obtain the ultrasound image of the target object. The ultrasound images obtained by the processor 103 may be stored in the memory 105, and may be displayed on the display 104.

In the embodiments of the present disclosure, the display 104 of the ultrasound imaging device 10 may be a touch screen, a liquid crystal display, etc., or may be an independent display device such as a liquid crystal display, a television or the like independent of the ultrasound imaging device 10, or may be the display screen on an electronic device such as a mobile phone or a tablet, etc.

In the embodiments of the present disclosure, the memory 105 of the ultrasound imaging device 10 may be a flash memory card, a solid-state memory, a hard disk, or the like.

In the embodiments of the present disclosure, a computer-readable storage medium may also be provided, which may store multiple program instructions. After the multiple program instructions are called and executed by the processor 103, a part or all or any combination of the steps of the ultrasound imaging methods in the embodiments of the present disclosure may be achieved.

In one embodiment, the computer-readable storage medium may be the memory 105, which may be a non-volatile storage medium such as a flash memory card, a solid-state memory, a hard disk, or the like.

In the embodiments of the present disclosure, the processor 105 of the ultrasound imaging device 10 may be implemented by software, hardware, firmware or a combination thereof, and may use circuits, single or multiple application specific integrated circuits (ASIC), single or multiple general-purpose integrated circuits, single or multiple microprocessors, single or multiple programmable logic devices, a combination of the foregoing circuits or devices, or other suitable circuits or devices, such that the processor 105 can perform the steps of the ultrasound imaging methods in the embodiments.

Figure 2:
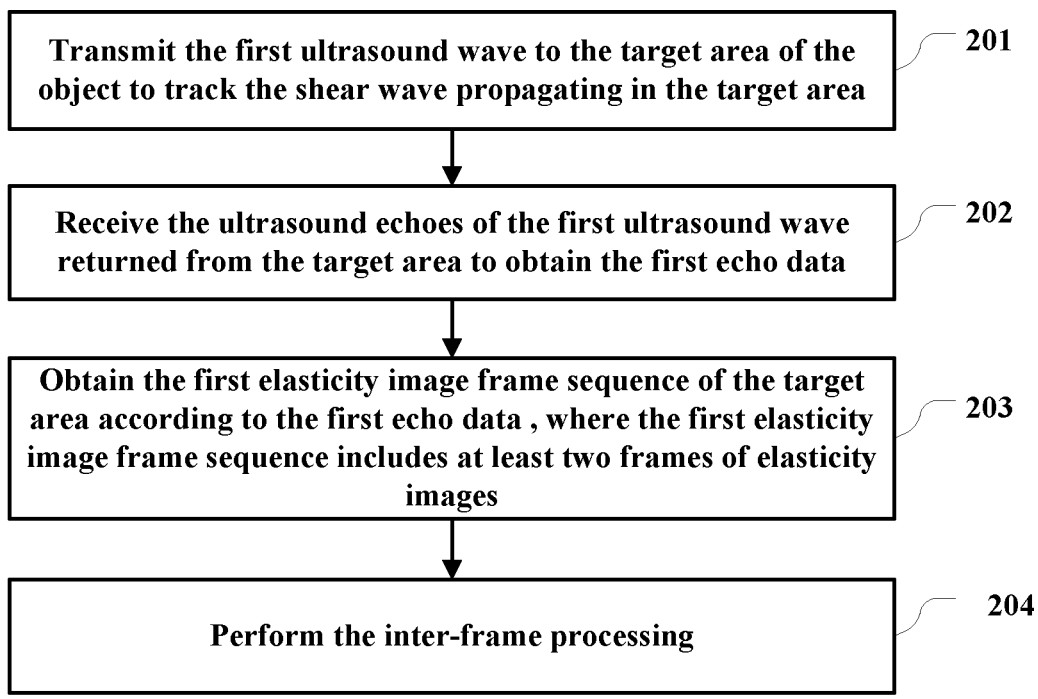
FIG. 2 is a schematic flow chart of the ultrasound imaging method in one embodiment.

The ultrasound imaging methods in the present disclosure will be described in detail below. Referring to FIG. 2, an ultrasound imaging method is provided by one embodiment of the present disclosure, which may be applied to the ultrasound imaging device 10, and be particularly suitable for an ultrasound imaging device 10 that includes a touch screen and can be operated by the inputs inputted through the touch screen. The ultrasound imaging device 10 may use the ultrasound echo data to generate elasticity images, and may also use the ultrasound echo data to generate conventional ultrasound B images or Doppler images. The ultrasound imaging method in one embodiment may include the following steps.

In step 201, a first ultrasound wave may be transmitted to a target area of the object to be examined to track a shear wave propagating in the target area.

In this embodiment, the ultrasound imaging device 10 may excite the ultrasound probe 100 through the transmitting/receiving sequence controller 102 to transmit the first ultrasound wave to the target area of the object to be examined to track the shear wave propagating in the target area. The target area may be determined according to the needs of the elasticity measurement. For example, the target area may be determined by detection using various applicable imaging modes such as conventional two-dimensional B-mode imaging, conventional elastography E-mode or the like, or may be selected according to the detection requirements.

In one embodiment, there may be one or multiple target areas. When there are multiple target areas, the longitudinal depths or lateral positions of the multiple target areas may be different.

The shear wave may be generated with the ways described below. In one embodiment, the shear wave may be generated by external vibration. For example, the external vibration may be used to generate the shear wave propagating into the tissue of the target area. Alternatively, the ultrasound pulse acoustic radiation force effect may be used to generate the shear waves in the tissue of the target area. Alternatively, the shear wave may be generated by the physiological movements of the tissue in the object to be examined (for example, the heartbeat, the blood vessel beat, etc.). Other ways may also be used. These ways will not be described in detail here. In the present disclosure, one commonly used method will be illustrated as an example: ultrasound shear wave elastography based on acoustic radiation force.

In the ultrasound shear wave elastography based on acoustic radiation force, the shear waves propagating in the target area may be generated by an ultrasound pulse with a specific waveform, length and frequency transmitted into the tissue by the ultrasound probe 100 excited by the transmitting/receiving sequence controller 102. The ultrasound pulse will produce acoustic radiation force effect inside the tissue, thereby generating the shear wave propagating in the tissue. A series of ultrasound waves may be transmitted to the tissue to track the propagation process of the shear wave in the tissue. It may also be possible to transmit the ultrasound pulse with a specific waveform, length and frequency to the tissue using another ultrasound device, in which the same effect can be achieved based on the acoustic radiation force effect generated by the ultrasound pulse.

In step 202, the ultrasound echoes of the first ultrasound wave returned from the target area may be received to obtain the first echo data.

In this embodiment, the processor 103 may control the ultrasound probe 100 through the transmitting/receiving sequence controller 102 to receive the ultrasound echoes of the first ultrasound wave returned from the target area to obtain the first echo data.

In step 203, a first elasticity image frame sequence of the target area may be obtained according to the first echo data. The first elasticity image frame sequence may include at least two frames of elasticity images.

In this embodiment, the processor 103 may process the first echo data obtained in step 202 to obtain at least two frames of elasticity images of the target area to obtain the elasticity image frame sequence.

In step 204, an inter-frame processing may be performed.

In this embodiment, the processor 103 may perform the inter-frame processing. The inter-frame processing process may include generating at least one frame of additional elasticity image according to the at least two frames of elasticity images to obtain a second elasticity image frame sequence, and displaying the second elasticity image frame sequence. The number of the frames of the second elasticity image frame sequence is greater than the number of the frames of the first elasticity image frame sequence.

It should be noted that the processor 103 may calculate the at least one frame of additional elasticity image according to the at least two frames of elasticity images obtained in step 203 to obtain the second elasticity image frame sequence. It should be noted that the second elasticity image frame sequence may include the at least one frame of additional elasticity image and all or part of the frames of the first elasticity image frame sequence, or include only the at least one frame of additional elasticity image. For example, the first elasticity image frame sequence may be E1, E2 while the second elasticity image frame sequence may be E1, EX, E2, where EX represents one frame of additional elasticity image in the at least one frame of additional elasticity image. For another example, the first elasticity image frame sequence may be E1, E2, E3 while the second elasticity image frame sequence may be E1, EX, EY, EZ, E3, where EX, EY, EZ represent three frames of additional elasticity images in the at least one frame of additional elasticity image. Since after the inter-frame processing process the number of the frames of the obtained second elasticity image frame sequence obtained is greater than the number of the frames of the original first elasticity image frame sequence, the display frame rate of the obtained second elasticity image frame sequence is higher than the display frame rate of the original first elasticity image frame sequence, thereby increasing the display frame rate of the elasticity images.

The elasticity image above may be combined with other mode of image so as to simultaneously realize the display of multiple imaging modes. For example, it may be combined with a B-mode, C-mode or PW-mode image, which will not be limited in this embodiment. For example, in combination with B-mode image, the elastography (hereinafter referred to as E-mode imaging) and B-mode imaging can be realized at the same time.

In one embodiment, the ultrasound imaging device 10 may excite the ultrasound probe 100 through the transmitting/receiving sequence controller 102 to transmit the second ultrasound wave to the target area of the object to be examined, and control the ultrasound probe 100 through the transmitting/receiving sequence controller 102 to receive the ultrasound echoes of the second ultrasound wave returned from the target area to obtain the second echo data. The second echo data may be used to achieve the B-mode imaging or C-mode imaging. The first echo data above may be used to achieve the E-mode imaging.

The processor 103 may process the obtained second echo data to obtain the B-mode image frame sequence or the C-mode image frame sequence of the target area, and control the display 104 to display the B-mode image frame sequence or the C-mode image frame sequence. In this way, B-mode imaging and E-mode imaging, or C-mode imaging and E-mode imaging, may be achieved.

Figure 3:
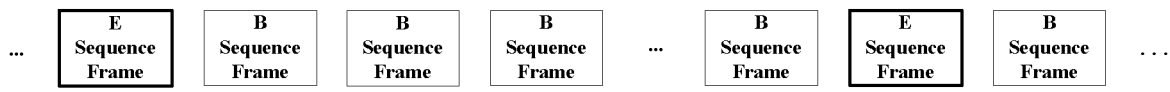
FIG. 3 is a schematic diagram of the transmitting/receiving frame sequence in one embodiment.

Taking simultaneously achieving the B-mode imaging and E-mode imaging as an example, the ultrasound imaging device 10 may transmit/receive at least two types of ultrasound sequence frames, such as a B sequence frame and an E sequence frame. The B sequence frame may refer to the ultrasound transmitting and receiving sequence used to generate one frame of conventional B-mode image, and the details of the imaging sequence will not be described herein. The E sequence frame may refer to the ultrasound transmitting and receiving sequence used to generate one frame of E image. Taking the shear wave elastography based on acoustic radiation force as an example, the E sequence frame may include the ultrasound pulse for generating the shear wave. Under the action of the ultrasound pulse, the shear wave will be generated to propagate in the tissue. Then a series of detection pulses may be transmitted to the target area in the tissue for a period of time, and the ultrasound echo signals may be received, which may be used to detect the propagation process of the shear wave in the tissue. Regarding the generation of the shear wave, reference may be made to the description in step 201, which will not be described in detail again here. The ultrasound echo signals of the B sequence frame may be used to obtain the B-mode image, and the ultrasound echo signals of the E sequence frame may be used to achieve the E-mode imaging to obtain E-mode image. In real-time imaging, the two sequence frames may be transmitted alternately. The transmitting frame rate of the B sequence frame may be different from that of the E sequence frame. Generally there are multiple B sequence frames between two adjacent E sequence frames. As shown in FIG. 3, each sequence frame may mean that one complete image may be obtained.

There are many ways for generating the at least one frame of additional elasticity image to obtain the second elasticity image frame sequence, which will not be limited in this embodiment. For example, interpolation or fixed weighting coefficients set by the system may be used to generate the at least one frame of additional elasticity image between the adjacent elasticity images in the first elasticity image frame sequence.

In one embodiment, the processor 103 may determine a first elasticity image and a second elasticity image from at least two elasticity images in the first elasticity image frame sequence. The first elasticity image and the second elasticity image may or may not be adjacent.

The processor 103 may determine the time interval between the first elasticity image and the second elasticity image, and generate at least one frame of additional elasticity image according to the time interval between the first elasticity image and the second elasticity image, so as to obtain the second elasticity image frame sequence.

In one embodiment, the time interval between the sequence frames may be the same. For example, the time interval between any two adjacent B sequence frames may be the same, and the time interval between any two adjacent E sequence frames may also be the same. But the two kinds of time intervals may be different. Therefore, in FIG. 3, taking the B sequence frame as an example, the time interval is the same regardless of whether an E sequence frame is inserted between two adjacent B sequence frames. The shorter the time interval, the higher the transmitting frame rate. In one embodiment, the transmitting frame rate of the B sequence frame may be higher than the transmitting frame rate of the E sequence frame.

In one embodiment, the B sequence frame or the C sequence frame inserted between the E sequence frames may be used for interpolation calculation.

Generating the at least one frame of additional elasticity image according to the time interval between the first elasticity image and the second elasticity image may include:

determining the number of the frames of the B-mode image or the C-mode image corresponding to the first elasticity image and the second elasticity image; and generating the at least one frame of additional elasticity image according to the number of the frames of the B-mode image or the C-mode image and the time interval between the first elasticity image and the second elasticity image.

It should be noted that since the transmitting frame rate of the E sequence frame is low and each E sequence frame can correspondingly obtain one E-mode image, the display frame rate of the E-mode images will also be low. However, the transmitting frame rate of the B sequence frame may be higher than the transmitting frame rate of the E sequence frame, therefore the display frame rate of the B sequence frame is relatively higher.

Taking simultaneously achieving the B-mode imaging and the E-mode imaging as an example, the ultrasound imaging device 10 may synchronously display the obtained images corresponding to the adjacent B sequence frame and E sequence frame, so that the user can observe the B-mode image and the E-mode image at the same time. The B-mode image contains information about tissue structure, and the E-mode image contains information about tissue hardness. Therefore, most B-mode images will not have corresponding synchronous E-mode images.

Based on the scene above where the B-mode imaging and the E-mode imaging are achieved simultaneously, the processor 103 may determine that the number of the frames of the B-mode images corresponding to the first elasticity image and the second elasticity image may be the sum of the number of the b-mode images inserted between the first elasticity image and the second elasticity image, the number of the frames of the B-mode images adjacent to the first elasticity image and the number of the frames of the b-mode images adjacent to the second elasticity image.

Figure 4:
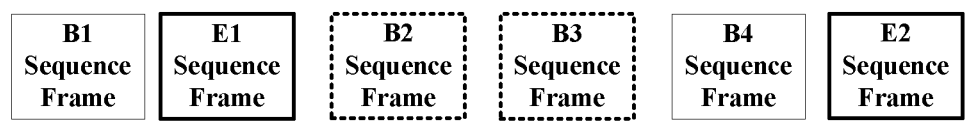
FIG. 4 is a schematic diagram of the inter-frame processing in one embodiment.

The first elasticity image and the second elasticity image may be two adjacent frames of E-mode images. The processor 103 may calculate the E sequence frames corresponding to the B sequence frames inserted between the two adjacent frames of E-mod images according to the two adjacent frames of E-mode images (hereinafter, referred to as the first E-mode image and the second E-mode image) or the echo data of the two E sequence frames and the number of the frames of the B-mode images corresponding to the first E-mode image and the second E-mode image. As shown in FIG. 4, assuming that the E1 sequence frame is the E sequence frame corresponding to the B1 sequence frame and the E2 sequence frame is the E sequence frame corresponding to the B2 sequence frame, there is no E sequence frames corresponding to the B2 sequence frame and the B3 sequence frame. Therefore, it is desired to calculate the E sequence frames corresponding to the B2 sequence frame and the B3 sequence frame through the inter-frame processing.

There are many methods for the inter-frame processing. The interpolation will be taken as an example. The times of the B sequence frames between two adjacent E sequence frames are known. The E sequence frames corresponding to the B sequence frames may be calculated based on the relationship between the times of the B sequence frames and the times of the two E sequence frame before and after the B sequence frames using the interpolation. As shown in FIG. 4, assuming that the time intervals between B1, B2, B3 and B4 sequence frames are all the same, the results of the interpolation calculation are as follows:

The E sequence frame corresponding to the B1 sequence frame is Enew1=E1;
The E sequence frame corresponding to the B2 sequence frame is Enew2=E1+(E2−E1)*1/3;
The E sequence frame corresponding to the B3 sequence frame is Enew3=E1+(E2−E1)*2/3;
The E sequence frame corresponding to the B4 sequence frame is Enew4=E2.

It can be seen that after the inter-frame processing, each B sequence frame has a corresponding E sequence frame, and the display frame rate of the E-mode images is increased to the same as the display frame rate of the B-mode images.

In the case that the time intervals between the B sequence frames are not the same, similar interpolation calculation may still be performed according to the length of the respective time intervals, which will not be described in detail here.

In the interpolation mentioned method, it may be possible that the target tissue may move during the imaging, resulting in a large displacement between the B sequence frames between two adjacent E sequence frames. In this case, the E sequence frame obtained by the interpolation only based on the time interval will not match the position of the B sequence frame well. Therefore, the tracking method may be used in the calculation. In one embodiment, generating the at least one frame of additional elasticity image according to the number of the frames of the B-mode images or the number of the frames of the C-mode images and the time interval between the first elasticity image and the second elasticity image may include:

determining the displacement of the target area according to at least two frames of the B-mode images or at least two frames of the C-mode images; and generating the at least one frame of additional elasticity image according to the number of the frames of the B-mode images or the number of the frames of the C-mode images, the displacement of the target area and the time interval between the first elasticity image and the second elasticity image.

It should be noted that the tracking method may be used to determine the displacement of the target tissue, and then the B-mode imaging and the E-mode imaging may be achieved simultaneously as described above. Using the tracking method, the displacement-related parameter between the B sequence frames may be calculated first. The E sequence frames may be adjusted according to the direction and amplitude of the displacement, and the interpolation may be performed according to the time interval. In the case that the position of the B2 sequence frame in FIG. 4 is changed relative to the B1 sequence frame, such as being translated as a whole by a certain distance, as shown in FIG. 5, when calculating the data point (such as the local data point in the figure) in the E sequence frame corresponding to the B2 sequence frame by interpolation, the E data information at the same position as such data point in the B1 and B4 sequence frames should be used for the interpolation.

Figure 5:
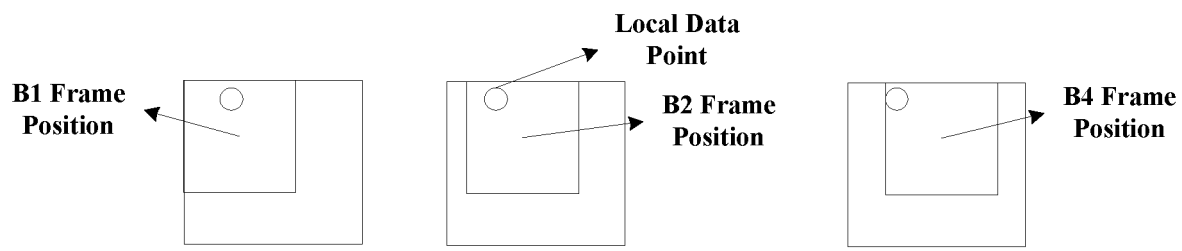
FIG. 5 is a schematic diagram of the frame shift in one embodiment.

What is shown in FIG. 5 is only an illustrative example. In actual applications, the directions and amplitudes of the displacements of at the positions of the local data points in the B sequence frame may be different. Therefore, the calculation for each local data point may be separately performed as needed.

Some other methods may also be used for the inter-frame processing, such as calculating the E sequence frame corresponding to the B sequence frame according to fixed weighting coefficients set by the system, etc. The present disclosure will not be limited to using the interpolation method. In one embodiment, generating the at least one frame of additional elasticity image according to the time interval between the first elasticity image and the second elasticity image may include:

generating the at least one frame of additional elasticity image according to the time interval between the first elasticity image and the second elasticity image and a preset weighting coefficient.

For example, a third E-mode image E3 and a fourth E-mode image E4 may be calculated using the preset weighting coefficients based on two adjacent elasticity images, i.e. the first E-mode image E1 and the second E-mode image E2. It can be seen that after the inter-frame processing, the number of the E sequence frames can be increased, and therefore, the display frame rate of the E-mode images can be increased. It should be noted that the method of generating at least one frame of additional elasticity image by preset weighting coefficients to increase the display frame rate may be applied to the simplex work mode. The simplex work mode may include the work mode of generating the B sequence frames to achieve the B-mode imaging, the work mode of generating C sequence frames to achieve the C-mode imaging, the work mode of generating E sequence frames to achieve the E-mode imaging, or the work mode of generating PW sequence frames to achieve the PW imaging.

When calculating the E sequence frame corresponding to the B sequence frame through the inter-frame processing, it is not necessary to calculate the E sequence frame for each B sequence frame. Rather, the E sequence frames may be calculated for only part of the B sequence frames. In this way, the number of the frames of the E sequence frames is still increased, so the display frame rate of the E-mode images will also be increased.

In one embodiment, in the ultrasound imaging device 10 of the present disclosure, in addition to generating B sequence frames and E sequence frames to achieve the B-mode imaging and the E-mode imaging at the same time, ultrasound sequences for color Doppler imaging may also be inserted so as to generate C sequence frames. The combination of various types of sequence frames will not be limited herein.

In the ultrasound imaging methods of the present disclosure, the new high frame rate E-mode images obtained by the inter-frame processing may be directly displayed during the real-time imaging. Alternatively, it may also be possible to display the original E-mode images first during the real-time imaging and start the display of the new high frame rate E-mode images obtained by the inter-frame processing by the user through the control button or key after the image acquisition is completed.

In one embodiment, after obtaining the first elasticity image frame sequence of the target area according to the first echo data, the method may further include:

displaying the first elasticity image frame sequence. The first elasticity image frame sequence may be the original E-mode images.

The inter-frame processing may include:

receiving a first operation, and performing the inter-frame processing according to the first operation. For example, the user may start the inter-frame processing through an operation such as pushing a control button or key or inputting a voice instruction to form the new high frame rate E-mode images, and display the new high frame rate E-mode images. The inter-frame processing here may be understood with reference to the description of step 204, and will not be described here again.

In one embodiment, the original E-mode image and the high frame rate E-mode image may also be switched freely. The ultrasound imaging method may further include:

receiving a first switching instruction, and performing the switch according to the first switching instruction. The switch may include: switching displaying the first elasticity image frame sequence to displaying the second elasticity image frame sequence, or switching displaying the second elasticity image frame sequence to displaying the first elasticity image frame sequence.

It should be noted that after the user starts the inter-frame processing through control button, key or voice instruction, etc. and the new high frame rate E-mode image are displayed, the user may further use button, key or voice instruction to switch displaying the new high frame rate E-mode images to displaying the original E-mode images. The displaying of the original E-mode images and the new high-frame rate E-mode images may be switched freely through button, key or voice instructions, etc., and the operation mode and switching frequency will not be limited here.

The ultrasound imaging methods of the present disclosure may also be suitable for other imaging modes where there are at least two different ultrasound sequence frames at the same time. For example, in the color flow mode in which there are B sequence frames and C sequence frames at the same time, the ultrasound imaging method of the present disclosure may be used to perform the inter-frame processing on the B sequence frames and/or C sequence frames to increase the display frame rate.

For another example, in the Doppler mode in which there are the B sequence frames and the PW sequence frame, the ultrasound imaging method of the present disclosure may be used to perform the inter-frame processing on the B sequence frames and/or the PW sequence frames to increase the display frame rate.

In the ultrasound imaging methods provided by the present disclosure, the ultrasound imaging device 10 may transmit the first ultrasound waves to the target area of the object to be examined through the transmitting/receiving sequence controller 102 to track the shear wave propagating in the target area, receive the returned ultrasound echoes of the first ultrasound waves to obtain the first echo data, obtain the first elasticity image frame sequence of the target area according to the first echo data by the processor 103, generate at least one frame of additional elasticity image according to at least two frames of elasticity images to obtain the second elasticity image frame sequence, and display the second elasticity image frame sequence. The second elasticity image frame sequence may be understood with reference to the relevant description of step 204 above, and will not be described here again. Since after the inter-frame processing process the number of the frames of the obtained second elasticity image frame sequence is greater than the number of the frames of the original first elasticity image frame sequence, the display frame rate of the obtained second elasticity image frame sequence is higher than that of the original first elasticity image frame sequence, thereby increasing the display frame rate of the elasticity images.

Figure 6:
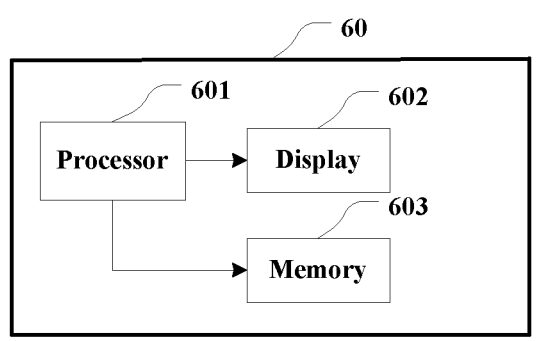
FIG. 6 is a schematic block diagram of another ultrasound imaging device in one embodiment.

FIG. 6 is a schematic block diagram of an ultrasound imaging device 60 in one embodiment. The ultrasound imaging device 60 may include a processor 601 and a display 602. The processor 601 may process the obtained ultrasound echo signals to obtain an ultrasound image of the target object. The ultrasound image obtained by the processor 601 may be stored in the memory 603, and may be displayed on the display 602.

In this embodiment, the display 602 of the ultrasound imaging device 60 may be a touch screen, a liquid crystal display, etc., or may be an independent display device such as a liquid crystal display or a television independent of the ultrasound imaging device 60, or may be a display screen of an electronic device such as a mobile phone, a tablet computer or the like.

In this embodiment, the memory 603 of the ultrasound imaging device 60 may be a flash memory card, a solid state memory, a hard disk, or the like.

In this embodiment, a computer-readable storage medium may also be provided, which may store multiple program instructions. After being called and executed by the processor 601, the multiple program instructions may perform a part or all or any combination of the steps of the ultrasound imaging methods in the embodiments of the present disclosure.

In one embodiment, the computer-readable storage medium may be the memory 603, which may be a non-volatile storage medium such as a flash memory card, a solid-state memory, a hard disk, or the like.

In the embodiments of the present disclosure, the processor 601 of the ultrasound imaging device 60 may be implemented by software, hardware, firmware or a combination thereof, and can use circuits, single or multiple application specific integrated circuits (ASIC), single or multiple general-purpose integrated circuits, single or multiple microprocessors, single or multiple programmable logic devices, a combination of the foregoing circuits or devices, or other suitable circuits or devices, such that the processor 601 can perform the steps of the ultrasound imaging methods in the embodiments above.

Figure 7:
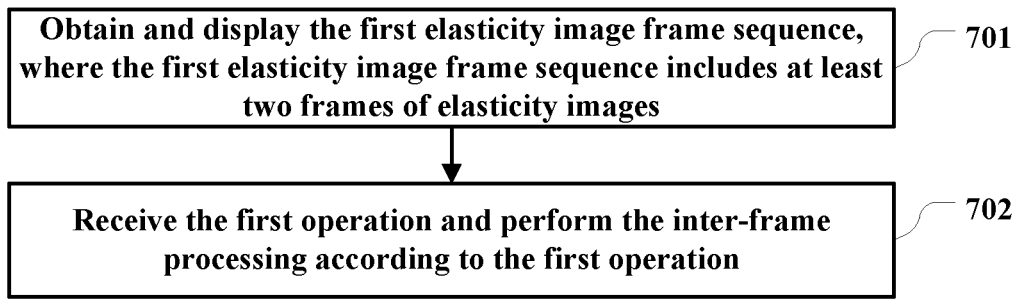
FIG. 7 is a schematic flow chart of another ultrasound imaging method in one embodiment.

The ultrasound imaging method in this embodiment will be described in detail below. Referring to FIG. 7, an ultrasound imaging method is provided by the present embodiment, which may be applied to the ultrasound imaging device 60, and particularly suitable for the ultrasound imaging device 60 that includes a touch screen and can be operated by the inputs inputted through the touch screen. The ultrasound imaging device 60 may use the ultrasound echo data to generate the elasticity images, and may also use the ultrasound echo data to generate the conventional ultrasound B images or Doppler images. The ultrasound imaging method may include the following steps.

Referring to FIG. 7, the ultrasound imaging method may include the following steps.

In step 701, the first elasticity image frame sequence may be obtained and displayed. The first elasticity image frame sequence may include at least two frames of elasticity images.

The first elasticity image frame sequence may be obtained by: transmitting the first ultrasound waves to the target area of the object to be examined through the ultrasound probe to track the shear wave propagating in the target area; receiving the ultrasound echoes of the first ultrasound waves returned from the target area to obtain the first echo data; and obtaining the first elasticity image frame sequence of the target area according to the first echo data. The first elasticity image frame sequence may be the elasticity images stored locally, or be the elasticity images obtained in real time. The ultrasound imaging device 60 may directly obtain the first elasticity image frame sequence stored locally, or may obtain the first elasticity image frame sequence through wired or wireless data transmitting. Further, the ultrasound imaging device 60 may control the display 602 to display the first elasticity image frame sequence.

In step 702, the first operation may be received, and the inter-frame processing may be performed according to the first operation.

The inter-frame processing may include: generating at least one frame of additional elasticity image according to at least two frames of elasticity images to obtain the second elasticity image frame sequence, and displaying the second elasticity image frame sequence, where the number of the frames of the second elasticity image frame sequence is greater than the number of the frames of the first elasticity image frame sequence. For example, the user may start the inter-frame processing through control buttons, keys or voice instructions to form the new high frame rate elasticity images, and the new high frame rate elasticity images may be displayed. The inter-frame processing may be understood with reference to the relevant description of step 204 in the embodiments above, and will not be described here again.

In the technical solutions provided by the embodiments of the present disclosure, the first elasticity image frame sequence may be obtained, and displayed, where the first elasticity image frame sequence may include at least two frames of elasticity images. The first operation may be received, and at least one frame of additional elasticity image may be generated according to at least two frames of elasticity images to obtain the second elasticity image frame sequence. The second elasticity image frame sequence may be displayed. The second elasticity image frame sequence may be understood with reference to the relevant description of step 204 above, and will not be described here again. Since after the inter-frame processing the number of the frames of the obtained second elasticity image frame sequence is greater than the number of the frames of the original first elasticity image frame sequence, the display frame rate of the obtained second elasticity image frame sequence is higher than that of the original first elasticity image frame sequence, thereby increasing the display frame rate of the elasticity images.

In one embodiment, the original elasticity image and the high frame rate elasticity image may also be switched freely. The ultrasound imaging method may further include:

receiving the first switching instruction, and performing the switch according to the first switching instruction. The switch may include switching displaying the first elasticity image frame sequence to displaying the second elasticity image frame sequence or switching displaying the second elasticity image frame sequence to displaying the first elasticity image frame sequence.

It should be noted that after the user start the inter-frame processing through the control button, key or voice instruction and the new high frame rate elasticity images are displayed, the user may further use button, key or voice instruction to switch displaying the new high frame rate elasticity images to displaying the original elasticity images. The original elasticity images and the new high frame rate elasticity images may be switched freely through button, key or voice instruction. The operation mode and the switching frequency will not be limited here.

Figure 8:
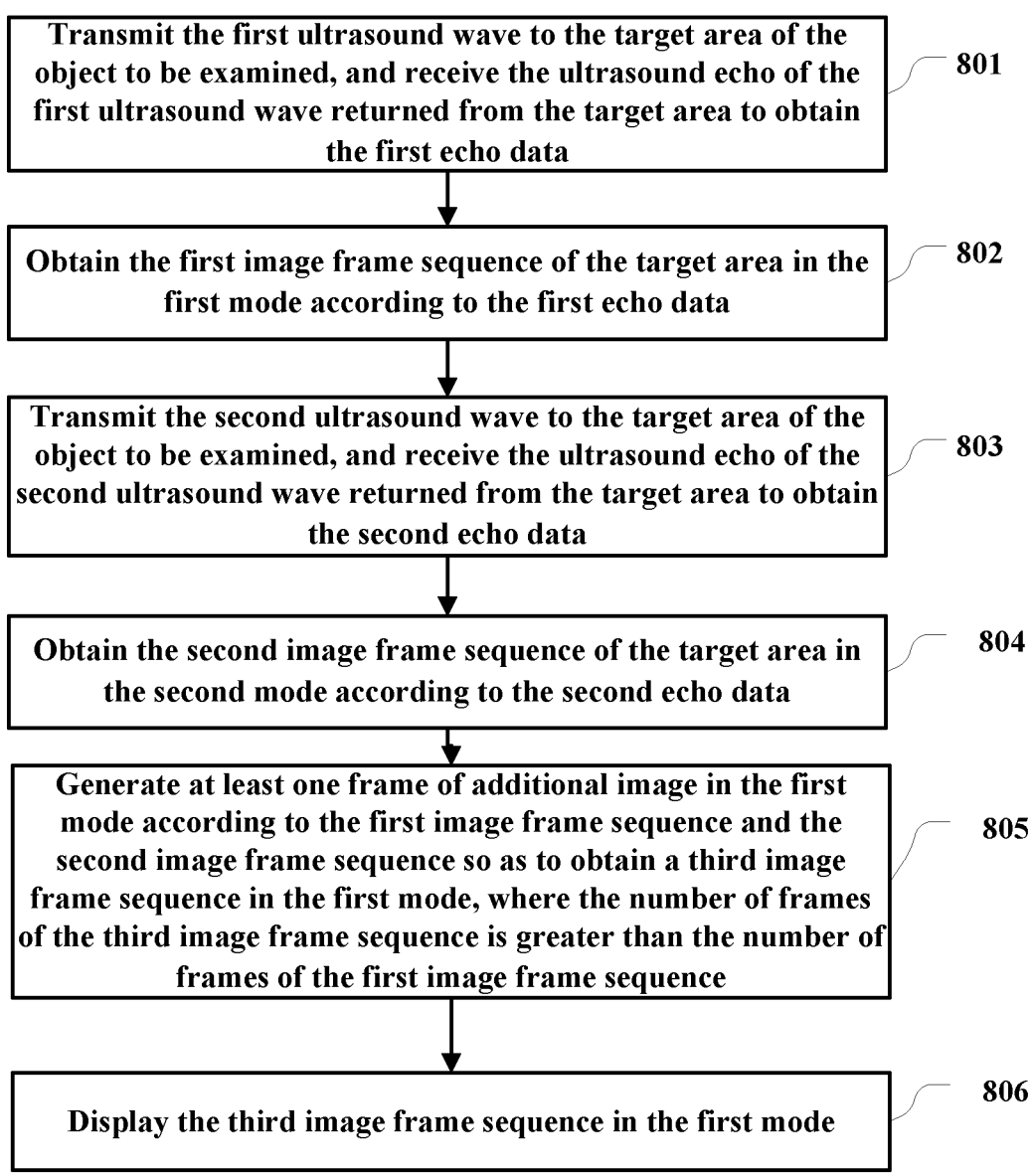
FIG. 8 is a schematic flow chart of another ultrasound imaging method in one embodiment.

The present disclosure also provides an ultrasound imaging method, which is applicable to the ultrasound imaging device 10. Referring to FIG. 8, the method may include the following steps.

In step 801, the first ultrasound waves may be transmitted to the target area of the object to be examined, and the ultrasound echoes of the first ultrasound waves returned from the target area may be received to obtain the first echo data.

In this embodiment, the ultrasound imaging device 10 may use the transmitting/receiving sequence controller 102 to excite the ultrasound probe 100 to transmit the first ultrasound waves to the target area of the object to be examined and receive the ultrasound echoes of the first ultrasound waves returned from the target area to obtain the first echo data.

In step 802, the first image frame sequence of the target area in a first mode may be obtained according to the first echo data.

In this embodiment, the processor 103 may process the first echo data obtained in step 802 to obtain at least two frames of elasticity images of the target area to form the first image frame sequence of the target area in the first mode.

In step 803, the second ultrasound waves may be transmitted to the target area of the object to be examined, and the ultrasound echoes of the second ultrasound waves returned from the target area may be received to obtain the second echo data.

In this embodiment, the ultrasound imaging device 10 may excite the ultrasound probe 100 through the transmitting/receiving sequence controller 102 to transmit the second ultrasound waves to the target area of the object to be examined, and receive the ultrasound echoes of the second ultrasound waves returned from the target area to obtain the second echo data.

In step 804, a second image frame sequence of the target area in a second mode may be obtained according to the second echo data.

In this embodiment, the processor 103 may process the second echo data obtained in step 803 to obtain at least two frames of elasticity images of the target area to form the second image frame sequence of the target area in the second mode.

The first mode and the second mode may be any two of the work mode of generating the B sequence frames to achieve the B-mode imaging, the work mode of generating the C-sequence frames to achieve the C-mode imaging, the work mode of generating the E sequence frames to achieve the E-mode imaging and the work mode of generating the PW sequence frames to achieve the PW imaging. For example, the first mode may be the work mode of generating the E sequence frames to achieve the E-mode imaging, while the second mode may be the work mode of generating the B sequence frames to achieve the B-mode imaging. For another example, the first mode may be the work mode of generating the C-sequence frames to achieve the C-mode imaging, while the second mode may be the work mode of generating the B sequence frames to achieve the B-mode imaging.

In step 805, at least one frame of additional image in the first mode may be generated according to the first image frame sequence and the second image frame sequence to obtain a third image frame sequence in the first mode, where the number of the frames of the third image frame sequence is greater than the number of the frames of the first image frame sequence.

In this embodiment, the processor 103 may calculate the at least one frame of additional image in the first mode according to the first image frame sequence and the second image frame sequence to obtain the third image frame sequence in the first mode. It should be noted that the third image frame sequence may include the at least one frame of additional image in the first mode and all or part of the first image frame sequence, or include only the at least one frame of additional image in the first mode. For example, the first image frame sequence may be E1, E2. The third image frame sequence may be E1, EX, E2, where EX represents one frame of additional image in the at least one frame of additional image in the first mode. For another example, the first image frame sequence may be E1, E2, E3. The third image frame sequence may be E1, EX, EY, EZ, E3, where EX, EY and EZ represent three frames of additional images in the at least one frame of additional image in the first mode. Since after the inter-frame processing, the number of the frames of the obtained third image frame sequence is greater than the number of the frames of the original first image frame sequence, the display frame rate of the obtained third image frame sequence is higher than that of the original first image frame sequence, thereby increasing the display frame rate of the ultrasound images.

In step 806, the third image frame sequence in the first mode may be displayed.

The processor 103 may control the display 104 to display the third image frame sequence in the first mode.

The embodiments above may be implemented entirely or partly by software, hardware, firmware or any combination thereof. When implemented by software, they can be implemented entirely or partly in the form of a computer program product.

The computer program product may include one or more computer instructions. When the computer instructions are loaded and executed in the computer, the processes or functions described in the embodiments of the present disclosure may be generated in whole or in part. The computer may be a general-purpose computer, a special-purpose computer, a computer network, or other programmable devices. The computer instructions may be stored in a computer-readable storage medium, or be transmitted from one computer-readable storage medium to another computer-readable storage medium. For example, the computer instructions may be transmitted from a website, computer, server or data center to another website, computer, server or data center via wired (such as coaxial cable, optical fiber, Digital Subscriber Line (DSL)) or wireless (such as infrared, wireless, microwave, etc.) connection. The computer-readable storage medium may be any available medium that can be used for storing by a computer or a data storage device such as an integrated server or data center which include one or more available media. The available medium may be a magnetic medium (such as a floppy disk, a hard disk, a magnetic tape), an optical medium (such as a DVD), a semiconductor medium (such as a solid state hard disk (SSD) or the like.

Those skilled in the art can clearly understand that, regarding the specific working process of the system, device and unit described above, reference may be made to the corresponding processes in the methods described above, which, for the convenience and conciseness of the description, will not be repeated here.

It should be understood that in the embodiments of the present disclosure the disclosed systems, devices and methods may be implemented in other ways. For example, the devices described above are only illustrative. For example, the division of the units is only a logical function division, and there may be other divisions in actual implementation. For example, multiple units or components may be combined or be integrated into another system. Some features may be ignored or not implemented. In addition, the displayed or discussed mutual coupling or direct coupling or communication connection may be indirect coupling or communication connection through some interfaces, devices or units, and may be in electrical, mechanical or other forms.

The units described as separate components may or may not be physically separated. The components displayed as units may or may not be physical units, that is, they may be located in one place, or they may be distributed on multiple network units. Some or all of the units may be selected according to actual needs to achieve the objectives of the solutions of the embodiments.

In addition, the functional units in the embodiments of the present disclosure may be integrated into one unit. Alternatively, the units may exist alone physically. Alternatively, two or more units may be integrated into one unit. The integrated unit may be implemented in the form of hardware or software functional unit.

In the case that the integrated unit is implemented in the form of a software functional unit and sold or used as an independent product, it may be stored in a computer readable storage medium. Based on this understanding, the essential part or the part that contributes to the existing technology or all or part of the technical solutions of the present disclosure may be embodied in the form of a software product. The software product may be stored in a storage medium, and may include multiple instructions which may be used to make a computer device (which may be a personal computer, a server, or a network device, etc.) to execute all or part of the steps of the method described in the embodiments of the present disclosure. The storage media may include a U disk, a mobile hard disk, a read-only memory (ROM), a random access memory (RAM), a magnetic disk, an optical disk or other media that can store program code.

The embodiments above are only used to illustrate, but not limit, the technical solutions of the present disclosure. Although the present disclosure has been described in detail with reference to the embodiments above, those of ordinary skill in the art should understand that the technical solutions in the embodiments may be modified or some of the technical features may be equivalently replaced. These modifications or replacements will not cause the essence of the corresponding technical solutions to deviate from the spirit and scope of the technical solutions in the embodiments of the present disclosure.

The invention claimed is:

1. An ultrasound imaging method, comprising:
    transmitting a first ultrasound wave and a second ultrasound wave alternately to a target area of an object to be examined;
    receiving an ultrasound echo of the first ultrasound wave returned from the target area to obtain first echo data and an ultrasound echo of the second ultrasound wave returned from the target area to obtain second echo data;
    obtaining a first elasticity image frame sequence of the target area according to the first echo data and a B-mode image frame sequence of the target area according to the second echo data, wherein the first elasticity image frame sequence comprises at least two frames of elasticity images; and
    performing an inter-frame processing, wherein the inter-frame processing comprises:
        determining a first elasticity image and a second elasticity image from the at least two frames of elasticity images, wherein the first elasticity image and the second elasticity image are different and correspond to a first B-mode image and a second B-mode image of the B-mode image frame sequence, respectively, and wherein at least one additional B-mode image of the B-mode image frame sequence is inserted between the first elasticity image and the second elasticity image;
        determining a time interval from the first elasticity image to the second elasticity image in the first elasticity image frame sequence;
        determining a number of frames of the at least one additional B-mode image inserted between the first elasticity image and the second elasticity image;
        determining a direction and amplitude of a displacement of the target area according to the first B-mode image, the at least one additional B-mode image, and the second B-mode image;
        adjusting the first elasticity image and the second elasticity image according to the direction and the amplitude of the displacement;
        generating, according to the determined time interval, the determined number of frames of the at least one additional B-mode image, the adjusted first elasticity image, and the adjusted second elasticity image, at least one frame of additional elasticity image corresponding to the at least one additional B-mode image inserted between the first elasticity image and the second elasticity image;
        inserting the generated at least one frame of additional elasticity image into at least a portion of the first elasticity image frame sequence to obtain a second elasticity image frame sequence comprising the generated at least one frame of additional elasticity image and at least the portion of the first elasticity image frame sequence; and
        displaying the second elasticity image frame sequence, wherein a number of frames of the second elasticity image frame sequence is greater than a number of frames of the first elasticity image frame sequence.

2. The method of claim 1, further comprising: after obtaining the first elasticity image frame sequence of the target area according to the first echo data,
    displaying the first elasticity image frame sequence;
    wherein performing the inter-frame processing comprises:
    receiving a first operation and performing the inter-frame processing according to the first operation.

3. The method of claim 1, further comprising: before transmitting the first ultrasound wave to the target area of the object to be examined,
    generating a shear wave.

4. The method of claim 1, wherein generating the at least one frame of additional elasticity image corresponding to the at least one additional B-mode image inserted between the first elasticity image and the second elasticity image comprises:
    generating a respective one of the at least one frame of additional elasticity image corresponding to different ones of the at least one additional B-mode image inserted between the first elasticity image and the second elasticity image.

5. The method of claim 2, further comprising:
    receiving a first switching instruction; and
    displaying the second elasticity image frame sequence comprises, according to the first switching instruction, switching from displaying the first elasticity image frame sequence to displaying the second elasticity image frame sequence.

6. An ultrasound imaging method, comprising:
    obtaining a first elasticity image frame sequence of a target area and a B-mode image frame sequence of the target area, and displaying the first elasticity image frame sequence and the B-mode image frame sequence, wherein the first elasticity image frame sequence comprises at least two frames of elasticity images;
    performing an inter-frame processing, wherein the inter-frame processing comprises:
        determining a first elasticity image and a second elasticity image from the at least two frames of elasticity images, wherein the first elasticity image and the second elasticity image are different and correspond to a first B-mode image and a second B-mode image of the B-mode image frame sequence, respectively, and wherein at least one additional B-mode image of the B-mode image frame sequence is inserted between the first elasticity image and the second elasticity image;

determining a time interval from the first elasticity image to the second elasticity image in the first elasticity image frame sequence;

determining a number of frames of the at least one additional B-mode image inserted between the first elasticity image and the second elasticity image;

determining a direction and amplitude of a displacement of the target area according to the first B-mode image, the at least one additional B-mode image, and the second B-mode image;

adjusting the first elasticity image and the second elasticity image according to the direction and the amplitude of the displacement;

generating, according to the determined time interval, the determined number of frames of the at least one additional B-mode image, the adjusted first elasticity image, and the adjusted second elasticity image, at least one frame of additional elasticity image corresponding to the at least one additional B-mode image inserted between the first elasticity image and the second elasticity image;

inserting the generated at least one frame of additional elasticity image into at least a portion of the first elasticity image frame sequence to obtain a second elasticity image frame sequence comprising the generated at least one frame of additional elasticity image and at least the portion of the first elasticity image frame sequence; and displaying the second elasticity image frame sequence, wherein a number of frames of the second elasticity image frame sequence is greater than a number of frames of the first elasticity image frame sequence.

7. The method of claim 6, further comprising:
receiving a first switching instruction, and performing a switch according to the first switching instruction;
wherein the switch comprises switching from displaying the first elasticity image frame sequence to displaying the second elasticity image frame sequence.

8. An ultrasound imaging device, comprising:
an ultrasound probe configured to transmit a first ultrasound wave and a second ultrasound wave alternately to a target area of an object to be examined;
a controller configured to receive an ultrasound echo of the first ultrasound wave returned from the target area to obtain first echo data and an ultrasound echo of the second ultrasound wave returned from the target area to obtain second echo data;
a processor configured to:
 obtain a first elasticity image frame sequence of the target area according to the first echo data and a B-mode image frame sequence of the target area according to the second echo data, wherein the first elasticity image frame sequence comprises at least two frames of elasticity images; and
 perform an inter-frame processing, wherein the inter-frame processing comprises:
  determining a first elasticity image and a second elasticity image from the at least two frames of elasticity images, wherein the first elasticity image and the second elasticity image are different and correspond to a first B-mode image and a second B-mode image of the B-mode image frame sequence, respectively, and wherein at least one frame of additional B-mode image of the B-mode image frame sequence is inserted between the first elasticity image and the second elasticity image;
  determining a time interval from the first elasticity image to the second elasticity image in the first elasticity image frame sequence;
  determining a number of frames of the at least one additional B-mode image inserted between the first elasticity image and the second elasticity image;
  determining a direction and amplitude of a displacement of the target area according to the first B-mode image, the at least one additional B-mode image, and the second B-mode image;
  adjusting the first elasticity image and the second elasticity image according to the direction and the amplitude of the displacement;
  generating, according to the determined time interval, the determined number of frames of the at least one additional B-mode image, the adjusted first elasticity image, and the adjusted second elasticity image, at least one frame of additional elasticity image corresponding to the at least one additional B-mode image inserted between the first elasticity image and the second elasticity image;
  inserting the generated at least one frame of additional elasticity image into at least a portion of the first elasticity image frame sequence to obtain a second elasticity image frame sequence comprising the generated at least one frame of additional elasticity image and at least the portion of the first elasticity image frame sequence; and
a display configured to display the second elasticity image frame sequence, wherein a number of frames of the second elasticity image frame sequence is greater than a number of frames of the first elasticity image frame sequence.

9. The ultrasound imaging device of claim 8, wherein:
the display is further configured to display the first elasticity image frame sequence; and
performing the inter-frame processing comprises receiving a first operation and performing the inter-frame processing according to the first operation.

10. The ultrasound imaging device of claim 8, wherein the ultrasound probe is further configured to generate a shear wave.

11. The ultrasound imaging device of claim 9, wherein the processor is further configured to:
receive a first switching instruction and perform a switch according to the first switching instruction;
wherein the switch comprises switching from displaying the first elasticity image frame sequence to displaying the second elasticity image frame sequence.

* * * * *

UNITED STATES PATENT AND TRADEMARK OFFICE
CERTIFICATE OF CORRECTION

| | |
|---|---|
| PATENT NO. | : 11,813,117 B2 |
| APPLICATION NO. | : 17/068744 |
| DATED | : November 14, 2023 |
| INVENTOR(S) | : Shuangshuang Li et al. |

It is certified that error appears in the above-identified patent and that said Letters Patent is hereby corrected as shown below:

In the Claims

Claim 8, Column 20, Lines 4-5:
"wherein at least one frame of additional B-mode image" should read -- wherein at least one additional B-mode image --.

Signed and Sealed this
Twenty-seventh Day of February, 2024

Katherine Kelly Vidal
*Director of the United States Patent and Trademark Office*